US00PP09850P

United States Patent [19]

Friday

[11] Patent Number: Plant 9,850

[45] Date of Patent: Apr. 8, 1997

[54] PEACH TREE 'P.F. 5B'

[75] Inventor: Paul J. Friday, P.O. Box 850, Coloma, Mich. 49038

[73] Assignee: Paul J. Friday, Coloma, Mich.

[21] Appl. No.: 585,712

[22] Filed: Jan. 16, 1996

[51] Int. Cl.[6] ..... A01H 5/00

[52] U.S. Cl. ..... Plt./43.1

[58] Field of Search ..... Plt./43.1

*Primary Examiner*—James R. Feyrer

*Attorney, Agent, or Firm*—Fred P. Kostka

[57] ABSTRACT

A new and distinct variety of peach *Prunus persica,* tree having the following unique combination of desirable features:

1. The new and distinct variety of peach tree is of moderate upright growth and a regular and productive bearer of semi-cling peaches.
2. Producing a very firm fruit having a resilient flesh texture.
3. A substantially spherical fruit with an attractive red skin coloring over a majority of the surface.
4. Very early maturing fruit of good taste.
5. A very early maturing fruit of good storage and shelf life.

1 Drawing Sheet

ORIGIN OF VARIETY

The new peach tree (hereinafter referred to as the P.F. 5B peach tree) was originated by Paul Friday in the experimental orchard, which is maintained for the purpose of breeding peach trees, at Paul Friday Farms Inc., located in Coloma, Mich. Coloma is located in the southwest section of Michigan.

In an ongoing mass selection breeding program, superior seedlings of unrecorded parentage are maintained as seed sources for the production of seeds which are collected and planted in mass. The seed producing parent trees are maintained solely as proprietary trees for breeding purposes and have not been released from the experimental orchard, where such trees can be evaluated for their adaptability to local and regional growing conditions. Seeds resulting from open pollination of the trees in the experimental orchard are regularly planted in mass to produce new populations of seedlings which are cultured and monitored to maturity. Trees with superior attributes are retained for further observation and testing, and contribute seeds to advancing generations of new populations of seedlings.

The tree of this application, P.F. 5B, was a selection from one such a seedling population, and was based on the numerous superior genetic attributes of this tree which are described in the botanical descriptions to follow. The botanical descriptions to follow are believed to represent a reasonably complete botanical description, of the new peach tree, which is sufficiently detailed to distinguish the tree from the most closely related trees within the same market class.

ASEXUAL REPRODUCTION OF THE VARIETY

The new and distinct variety of peach tree was asexually propagated by budding as performed in the experimental orchard of Paul Friday Farms Inc., located in Coloma, Mich. The asexual propagation demonstrates that such reproduction of the characteristics of the tree are consistent and are established and transmitted through succeeding propagation.

SUMMARY OF THE VARIETY

The new and distinct variety of peach tree is of moderate upright growth and a regular and productive bearer of peaches. The P.F. 5B peach tree bears a semi-cling peach of large diameter of about 2½". The peach is characterized by a shallow suture. The skin color is an attractive red which extends in mottled form and stripes into an underlying yellow background. The blossoms are characterized by being contracted or partially spread when in full bloom. At the same time the petals of the blossoms are of lesser length than the length of petals of the normal showy blossom as exemplified by the Loring peach blossom.

The flesh of the fruit of the present peach tree is firm and is a dull pale yellow. The flesh surrounding the pit is of minimal color. At maturity the peach is spherical having an average diameter of about 2½".

The fruit has a firm flesh and may be described as resilient to the extent that the flesh is yieldable and restorable to its original state when subjected to impact forces which may cause permanent deformities in peaches of the commercial varieties. The firmness of the fruit facilitates handling and packaging of the peaches without damaging the same for shipment. This results in less spoilage and also increases the shelf life.

The fruit matures in the very early part of the peach growing season of southwestern Michigan. The fruit as mentioned heretofore is of pleasing red color over a substantial portion of its surface and has a very attractive appearance.

BRIEF DESCRIPTION OF THE PHOTOGRAPHS

In the drawing, the top photograph, taken at a maturity stage of firm ripe for harvest on Jul. 22, 1995, shows typical branch of wood of fruiting age, with three specimens of fruit attached at different angles. The rounded fruit shape, very shallow suture, exceptional symmetry; and, the color of the solid blush and mottled over-color pattern are depicted over the ground color of the fruit skin. An additional, separated specimen of the fruit is depicted in an orientation showing the stem end and coloration of the fruit at the stem end. A fifth specimen of fruit, which has been bisected on the suture plane, is also presented in the top photograph to illustrate the essentially uniform flesh color, a portion of the stone, the light color of the flesh adjacent to the stone, and the stone color. A tape measure is positioned over the bisected fruit to indicate the size of the fruit and the stone. A twig of current season's growth is also shown in this view.

In the bottom figure of the drawing, a stem of fruiting wood is depicted at a stage of full bloom with leaf break; and shows bark coloration, the shape, color and character of the blossoms, and that two blossoms are normally presented at each node.

DESCRIPTION OF VARIETY

The detailed botanical description of the foliage and fruit of the new variety of peach tree is based upon observations of the specimens grown at Coloma, Mich. with the color terminology, other than the terminology expressed in common terms, in accordance with the Panatone Matching System (PMS) as used internationally to identify printed colors.

Tree:
- *Height.*—Unpruned 16'.
- *Width.*—Unpruned 13'.
- *Size.*—Medium to large.
- *Vigor.*—Medium vigor terminal growth of approximately 18" per year.
- *Density.*—Medium.
- *Form.*—Upright.
- *Production.*—Productive, approximately ½ of the fruit annually must be thinned off to obtain size described.
- *Bearer.*—Consistent.
- *Disease resistance to bacterial leaf and fruit spot.*—Somewhat resistant.

Trunk:
- *Size.*—Medium.
- *Surface.*—Smooth.

Branches:
- *Size.*—Medium.
- *Surface.*—Smooth.

*Lenticels.*—Medium to many, average size ¼" long.
- *Color.*—Gray.

Leaves:
- *Size.*—Medium. Average length — 5", average width — 1".
- *Form.*—Lanceolate — pointed.
- *Thickness.*—Medium.
- *Texture.*—Medium.
- *Margin.*—Serrate.
- *Petiole.*—Medium length — medium thickness.
- *Glands.*—Usually 1 to 2 on each side of the basal portion of the leaf lamina at the juncture of the petiole and/or on the petiole adjacent the juncture.
- *Color.*—Upper surface: green (350c). Bottom: dull green (349c).

Flower buds:
- *Size.*—Medium.
- *Length.*—Medium.

Flowers:
- *Blooming period.*—May 1, 1995 to May 6, 1995.
- *Size.*—Slightly showy, about 1" diameter.
- *Pollen.*—Present, self-fertilizing.
- *Color.*—Pink.

Fruit:
- *Maturity when described.*—Firm ripe.
- *Date of first picking.*—Jul. 20, 1995 (about 3 weeks before the Red Haven peach). Fruit matures very evenly and can be harvested in two pickings.
- *Date of last picking.*—Jul. 29, 1995.
- *Size.*—Medium to large sphere. Average diameter — 2½".
- *Form.*—Spherical.
- *Suture.*—Very shallow.

Skin:
- *Thickness.*—Medium.
- *Texture.*—Tough — Tenacious to skin.
- *Tendency to crack.*—None.
- *Down.*—Little.
- *Color.*—Red overlying a yellow background with red extending as stripes or mottled into the background (1945c).

Flesh:
- *Texture.*—Firm — non-melting.
- *Ripens.*—Relatively even.
- *Flavor.*—Excellent.
- *Aroma.*—Pleasant.
- *Eating quality.*—Excellent.
- *Color.*—Somewhat dull pale yellow (127u), minimal color around pit.

Stone:
- *Type.*—Semi-cling.
- *Size.*—Average length — 1⅛". Average width — 1". Average thickness — ¾".
- *Form.*—Ovid.
- *Base.*—Straight.
- *Apex.*—Rounded.
- *Sides.*—One side tapers on base end.
- *Surface.*—Shallow furrows.
- *Color.*—Light tan (719c).
- *Tendency to crack.*—Moderate.

Use: Desert.
Shipping quality: Good.
Keeping quality: Good.

The tree and its fruit herein described may very in slight detail as a result of differences in climatic or soil conditions or cultural practices under which the tree may be grown. It is to be understood that the description of the new variety as set forth herein is that of the tree grown under the ecological conditions prevailing at Coloma, Mich.

What is claimed is:

1. A new and distinct variety of peach tree substantially as illustrated and described as a medium size tree, a consistent bearer of pleasingly colored, large fruit for the very early peach growing season, said fruit being a semi-cling peach and at maturity being of spherical shape with firm flesh and red skin color.

* * * * *

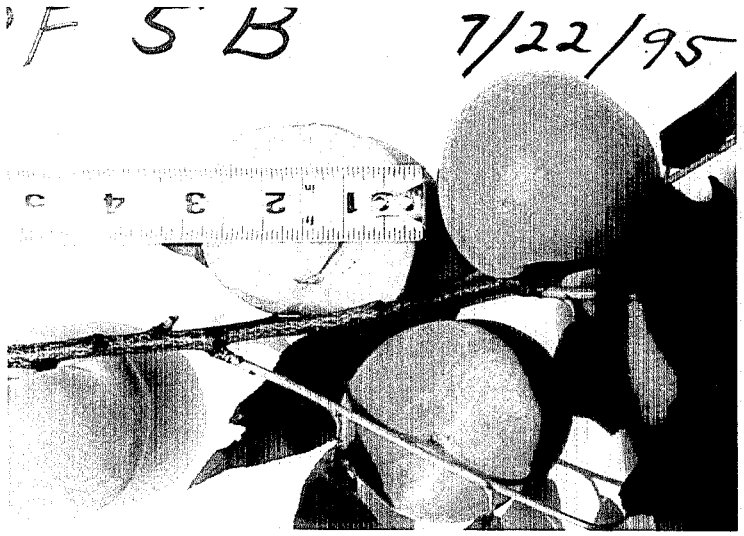
F 5 B
7/22/95
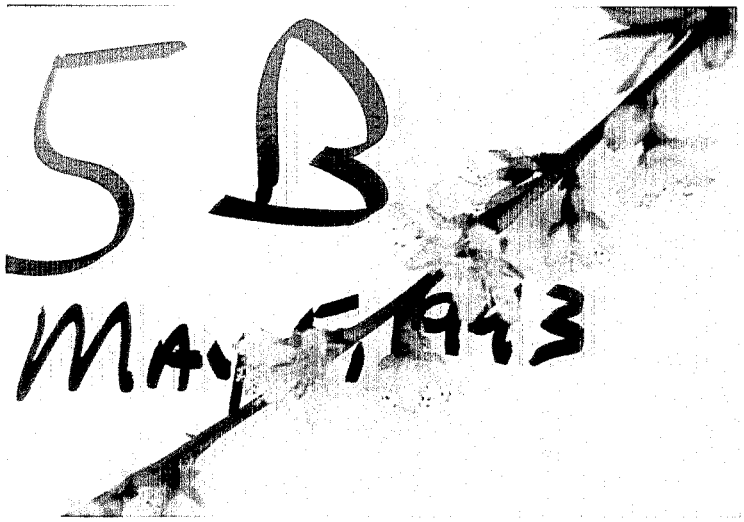
5 B
MAY 5, 1993